United States Patent
Perumalla et al.

(10) Patent No.: US 12,381,003 B2
(45) Date of Patent: Aug. 5, 2025

(54) DIGITIZING DISEASE SYMPTOMS

(71) Applicant: International Business Machines Corporation, Armonk, NY (US)

(72) Inventors: Saraswathi Sailaja Perumalla, Visakhapatnam (IN); Venkata Vara Prasad Karri, Visakhapatnam (IN); Shanthan Chamala, Malvern, PA (US); Amit Kumar Senapaty, Visakhapatnam (IN); Sarbajit K. Rakshit, Kolkata (IN)

(73) Assignee: International Business Machines Corporation, Armonk, NY (US)

( * ) Notice: Subject to any disclaimer, the term of this patent is extended or adjusted under 35 U.S.C. 154(b) by 699 days.

(21) Appl. No.: 17/223,715

(22) Filed: Apr. 6, 2021

(65) Prior Publication Data
US 2022/0319700 A1    Oct. 6, 2022

(51) Int. Cl.
*G16H 50/00* (2018.01)
*A61B 5/00* (2006.01)
*G16H 10/60* (2018.01)
*G16H 20/00* (2018.01)
*G16H 50/20* (2018.01)

(52) U.S. Cl.
CPC ............ *G16H 50/20* (2018.01); *A61B 5/6801* (2013.01); *A61B 5/7246* (2013.01); *A61B 5/742* (2013.01); *G16H 10/60* (2018.01); *G16H 20/00* (2018.01)

(58) Field of Classification Search
None
See application file for complete search history.

(56) References Cited

U.S. PATENT DOCUMENTS

| 4,975,842 A | 12/1990 | Darrow |
| 2008/0058664 A1 | 3/2008 | Mirro |
| 2012/0029303 A1* | 2/2012 | Shaya .................. G16H 50/20 348/E7.083 |
| 2013/0085538 A1 | 4/2013 | Volpe |
| 2015/0310183 A1* | 10/2015 | Madhavan ............ G16H 40/67 705/2 |
| 2019/0198169 A1* | 6/2019 | T ......................... G06F 16/951 |

OTHER PUBLICATIONS

Anonymous. "Healthcare Training Using a Robot Digital Twin and Augmented Reality." Published Mar. 6, 2020. 6 pages. Published by IP.com. https://priorart.ip.com/IPCOM/000261461.

Anonymous. "System and Method of Identifying Contagion Exposure through Social Interactions Analysis." Published Dec. 24, 2016. 6 pages. Published by IP.com. https://priorart.ip.com/IPCOM/000248673.

(Continued)

*Primary Examiner* — Sana Sahand
(74) *Attorney, Agent, or Firm* — Zilka-Kotab, P.C.

(57) ABSTRACT

The present disclosure includes digitizing user symptoms. A processor may receive user provided data from one or more data collection devices. A processor may access a historical database. The historical database may include historical user provided data. A processor may generate a user data packet based, at least in part on, the user provided data and the (Continued)

historical database. A processor may display the user data packet to one or more authorized user and one or more other correlating information.

16 Claims, 5 Drawing Sheets

(56) References Cited

OTHER PUBLICATIONS

Anonymous. "System to Recommend More Suitable Medications and Dosages." Published Jun. 28, 2019. 7 pages. Published by IP.com. https://priorart.ip.com/IPCOM/000258970.

Anonymous. "Virtual Worlds method to visually track the progression of a condition and create recommendations." Published May 8, 2009. 5 pages. Published by IP.com. https://priorart.ip.com/IPCOM/000182913.

Chambers, et al., "Digital and online symptom checkers and health assessment/triage services for urgent health problems: systematic review." Published Jul. 2, 2019. 13 pages. Published by BMJ Open. https://bmjopen.bmj.com/content/9/8/e027743.

Esposito, L., "How to Describe Medical Symptoms to Your Doctors." Published May 8, 2014. Printed Feb. 16, 2021. 6 pages. Published by US News. https://health.usnews.com/health-news/patient-advice/articles/2014/05/08/how-to-describe-medical-symptoms-to-your-doctors.

Felman, A., "Why do signs and symptoms matter?" Published Feb. 22, 2018. Printed Feb. 16, 2021. 12 pages. Published by Medical News Today. https://www.medicalnewstoday.com/articles/161858.

Jahns, R., "Next generation of symptoms checkers will become one of the killer applications in digital health." Printed Feb. 16, 2021. 7 pages. Published by Research 2 Guidance. https://research2guidance.com/next-generation-of-symptoms-checkers-will-become-one-of-the-killer-applications-in-digital-health/.

Mell, et al., "The NIST Definition of Cloud Computing," Recommendations of the National Institute of Standards and Technology, U.S. Department of Commerce, Special Publication 800-145, Sep. 2011, 7 pgs.

Pascual, C., "The Digitization Of Healthcare Is A One-Way Street." Published Aug. 3, 17. Printed Feb. 16, 2021. 2 pages. Published by Health IT Outcomes. https://www.healthitoutcomes.com/doc/the-digitization-of-healthcare-is-a-one-way-street-0001.

Vanhouten, H., "The digital patient: will we one day have our own health avatars?" Published Dec. 11, 2018. Printed Feb. 16, 2021. 10 pages. Published by Philips. https://www.philips.com/a-w/about/news/archive/blogs/innovation-matters/20181211-the-digital-patient-will-we-one-day-have-our-own-health-avatars.html.

* cited by examiner

DIGITIZING DISEASE SYMPTOMS

BACKGROUND

The present disclosure relates generally to collecting symptoms from users, and more particularly to techniques to aid authorized users.

Authorized users (e.g., medical professionals) have traditionally had to balance long hours and a large user load, while still providing excellent user care. Often, during a medical examination, a doctor or other authorized user may only be able to interact with the user during a short time, during which the authorized user is dependent on the user to relay symptom information associated with their potential ailment. While accurate symptom information is often necessary or useful in determining an accurate diagnosis, there are often circumstances where a user may not provide the accurate or completed symptom information.

SUMMARY

Embodiments of the present disclosure include a method, computer program product, and system for digitizing user symptoms. A processor may receive user provided data from one or more data collection devices. A processor may access a historical database. The historical database may include historical user provided data. A processor may generate a user data packet based, at least in part on, the user provided data and the historical database. A processor may display the user data packet to one or more authorized user and one or more other correlating information.

The above summary is not intended to describe each illustrated embodiment or every implementation of the present disclosure.

BRIEF DESCRIPTION OF THE DRAWINGS

The drawings included in the present disclosure are incorporated into, and form part of, the specification. They illustrate embodiments of the present disclosure and, along with the description, serve to explain the principles of the disclosure. The drawings are only illustrative of certain embodiments and do not limit the disclosure.

Figure 1:
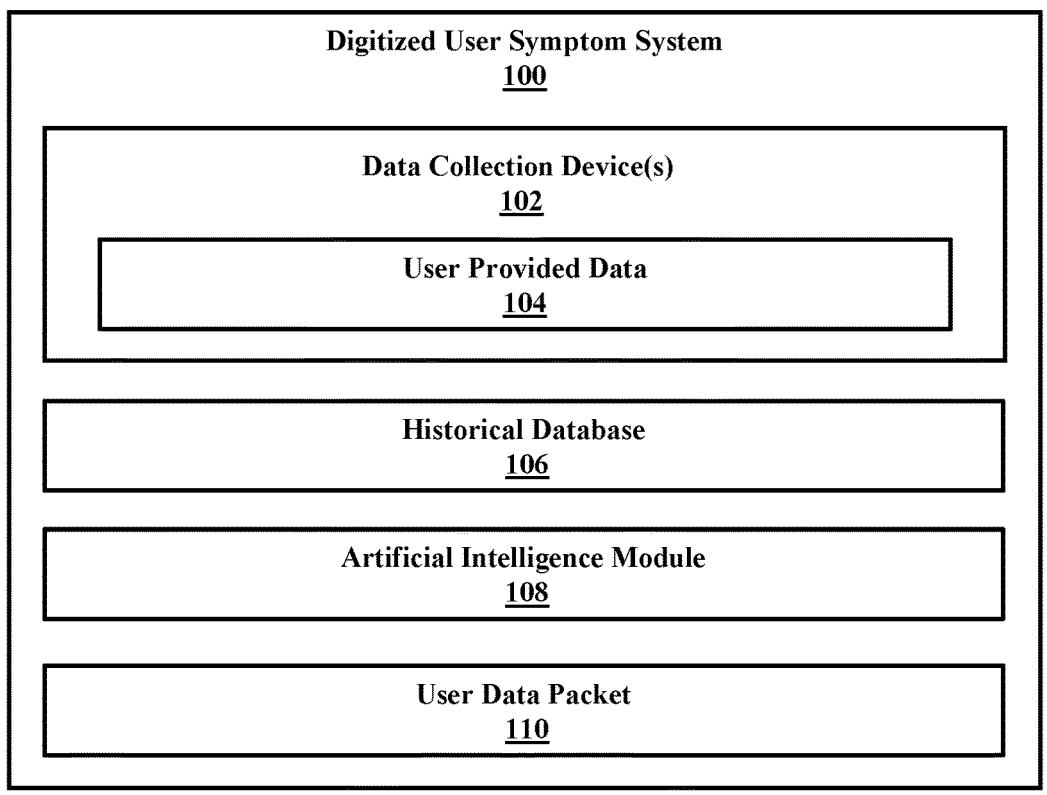
FIG. 1 illustrates a block diagram of a system for digitizing user symptoms, in accordance with embodiments of the present disclosure.

While the embodiments described herein are amenable to various modifications and alternative forms, specifics thereof have been shown by way of example in the drawings and will be described in detail. It should be understood, however, that the particular embodiments described are not to be taken in a limiting sense. On the contrary, the intention is to cover all modifications, equivalents, and alternatives falling within the spirit and scope of the disclosure.

DETAILED DESCRIPTION

The present disclosure relates generally to collecting symptoms from users, and more particularly to techniques to aid authorized users, such as digitizing user symptoms. While the present disclosure is not necessarily limited to such applications, various aspects of the disclosure may be appreciated through a discussion of various examples using this context.

While medical care and practices are be constantly evolving, authorized users often still depend on user provided information regarding their symptoms in order to make a diagnosis. While user symptom information indubitably useful, there may be various circumstances that prevent a authorized user from receiving correct and/or complete user symptoms. Such circumstances may include, but are not limited to, language barriers between user and doctor, a user not knowing that a particular observed body response is a symptom of a larger medical issue and as such does not relay the symptom to the authorized user, or a user who relies on a caretaker to communicate their symptoms to the authorized user. As such, there is a desire to more collect accurate and data from users that may be useful in diagnosing and treating their ailment.

In embodiments discussed herein, are solutions provided in the form of a method, system, and computer program product dynamically digitizing user symptoms, based on user provided/consented information. Embodiments contemplated herein leverage user provided data and historical user provided data with artificial intelligence (AI) to identify and digitize the user symptoms for authorized users.

In embodiments, a processor may receive or collect user provided data. In these embodiments, only data/information expressly authorized/consented to by a user or healthcare proxy (e.g., person authorized to make decisions regarding the user's medical care in the event the user is incapacitated) may be considered user provided data. In these embodiments, a user or healthcare proxy may optionally authorize and determine what specific information may be accessed by the processor. For example, a user may authorize a processor to collect/receive changes in the user's heartrate from a wearable heart monitor and may not authorize the processor to collect/receive changes to her $O_2$ levels. In this example, a processor would collect/receive user provided data associated with changes in the user's heartrate, but not data, even if the data could be collected from the same wearable device, would be collected/received by the processor associated with the user's $O_2$ levels. In some embodiments, user provided data may also include data/information from a user associated with an incapacitated user (e.g., caretaker). User provided data received from a caretaker (e.g., a person authorized to provide personal medial information of the user) may include any data/information they have collected as well as their caretaker's input based, at least in part on, their experience with the user.

In embodiments, a processor may receive or collect user provided data from one or more data sources. These data sources may include, but are not limited to, data feeds from wearable technology (e.g., bio-sensors, smart watch, smart ring, smart belt, smart glasses, and smart shoes), Internet of Things (IoT) sensor feeds configured to detect user provided data, video/audio monitoring, convolutional neural networks (CNN), or any combination of In these embodiments, user provided data may be stored in a historical database. In embodiments, a processor may utilize AI methods and techniques and the user provided data stored in the historical database to determine a user's standard baseline characteristics. A processor may then be configured to compare the current user provided data (e.g., user provided data in real-time) with the historical user provided data and determine if the user is exhibiting a symptom. For example, a processor may be configured to collect/receive a user's heartrate (e.g., user provided data). In this example, the processor may access the historical database and to determine (e.g., using machine learning and AI techniques) what the user's typical resting heartrate is. The processor may then compare current user provided data (e.g., the user's real-time heartrate) to the historical baseline and determine if the current heartrate is normal or if it is a potential user symptom of the user's ailment.

While the aforementioned example embodiment offers a simple example, such techniques may be much more complex and involve user provided data associated with amount of exercise, type of exercise, respiration changes during different activities, or any other type of data or information that may be useful in identifying a symptom and determining a diagnosis. In embodiments, a processor may identify the context of particular events that may have just occurred using user provided data. For example, a processor may identify that a user or user just started to drink from a cold beverage or that the user sneezed by noting a change in their breathing and/or heartrate. In some embodiments, a processor may identify an event type associated with user provided data. For example, a processor may identify that the weather/climate is during a particular day. In some embodiments, a processor may use user provided data (e.g., user's hair color and/or face shape) to generate an avatar or animated character configured to represent the user.

In embodiments, a processor may analyze the user data, using AI techniques, to determine one or more user symptoms. In embodiments, an AI may analyze user provided data to develop a knowledge graph. In these embodiments, a processor may extract relevant user symptoms from the user provided data. A processor may compile these user symptoms into a user data packet. A user data packet may also include other correlating data provided by the user. This correlating data may include information such as the duration of ailment/illness, precautionary steps taken, currently prescribed medications, and how the symptoms may have changed before and after the prescribed medication. In some embodiments, a processor may auto display (e.g., when the doctor opens the user data packet) or prompt the authorized user to reference one or more reports or digital medical records that may be necessary to review in order to diagnose or treat the user.

While in some embodiments a user data packet may be compiled or digitized and sent to an authorized user for review, in other embodiments, a user data packet may be custom tailored to the particular authorized user. In some embodiments, the user data packet is custom tailored based, at least in part, on the authorized user's medical discipline For example, if user A has a cardiologist and an ophthalmologist he is seeing a user data packet generated for a cardiologist may be custom tailored to include user symptoms associated with heart disease (e.g., arrythmia), while the user data packet for the ophthalmologist may be custom tailored to highlight user symptoms associated with the user's vision problems (e.g., increase in headaches).

In some embodiments, a processor may be configured to collect or receive an audio and/or video snippet from the user and compile it as part of the user data packet. In these embodiments, the audio and/or video snippet may allow the user to provide the authorized user a brief, but real-time elaborate view of the user. For example, a doctor could review the audio and/or video snippet of a user with a cough. From this snippet, the doctor could use his expert knowledge to study the duration of cough, type of cough, as well as if the user has any secondary symptoms to the cough (e.g., runny nose, irritated eyes).

In embodiments, user data packet may be configured to allow authorized users to interact with the user data packet. For example, a user's user data packet may be converted to a movie or audio media to allow the authorized user to immerse themselves in the user's symptoms. In these embodiments, the user data packet may be configured in any way that may enhance a authorized user's ability to diagnose and treat a user. As such, a processor may display and configure the user provided data in a variety of ways. These include, but are not limited to, zooming in/out, pausing, rewinding, note taking, as well as, providing additional reference material to the authorized user based, at least in part, on how authorized user interacts with the user data packet.

In some embodiments, a processor may convert the information contained in the data packets into audio and/or video snippets. The processor may send these data packets to one or more medical practitioner. These data packets may have real time detailed user data that can provide a detailed view and analysis of their disease state. For example, the data packet may include information such as, the duration of a cough, the type of cough, and does the user have additional disease symptoms like a running nose or irritated eyes.

In some embodiments, a processor may use the user data packet to generate a cross-sectional study of users with medically unexplained symptoms and explained symptoms. In some embodiments, the cross-sectional study may collect the number of times the authorized user viewed the user data packet, determine if the authorized user used any other digital features zoom in/out, or pause/start video), or whether the authorized user used a stylus to notate the user data packet. In embodiments, the processor generated cross-sectional studies may help classify user symptoms. In these embodiments, the processor may generate diagnostic strategies based on the user symptoms. In some embodiments a processor may classify user symptoms as either organic, functional, morbidity related, or genetic related.

In some embodiments, when a authorized user annotates a user data packet, a processor may generate a reference (e.g., and embedded webpage link) of a particular medical journal article, or previously solved cases e.g., published case studies). In some embodiments, a processor (e.g., using AI techniques) may suggest medications for similar symptoms. In these embodiments, in addition to suggesting medications, a processor may also generate additional medication information, such as how and where the medication is available and other information such as, the medication's availability in the pharmaceutical market and how quickly other users, who exhibited other symptoms, were returned to health once they utilized the medication. In some embodiments, a processor may recommend different disease symptoms (e.g., symptoms to consider and how they might be treated) that the authorized user may be comparable to the user's symptoms as well as other authorized users or doctors (e.g., experts who have encountered the illness or ailment before) who may be contacted for a second option regarding the user.

In some embodiments, a processor may perform one or more simulations using user provided data and the user data packet. These simulations may forecast one or more different scenarios about the user symptoms. For example, how likely is the user to respond to one specific medication versus another different medication. In some embodiments, the processor may display medical cases where other people exhibited symptoms similar or related to the user's symptoms, traditionally recommended medications associated similar user symptoms. In some embodiments, the processor displays the related medical cases while the authorized user is reviewing the user data packet (e.g., while the doctor is interacting with the audio/video of the user data packet). In these embodiments, a processor may dynamically correlate where the authorized user is viewing the user data packet (e.g., beginning, middle, or end) and the possibly, related medical cases. In some embodiments, the processor may generate and customize a report summarizing the authorized user's work with the user data packet.

In some embodiments, a processor may recommend one or more suggested diagnoses to the authorized user associated with the user's symptoms. In these embodiments, a processor may recommend one or more treatment plans associated with the one or more diagnosis. For example, the processor determines that a user is likely to have a particular diagnosis, the processor may recommend based, at least in part, on a user's medical history, a treatment plan.

Referring now to FIG. 1, a block diagram of a digitized user symptom system 100 for digitizing user data and generating a user data packet, is depicted in accordance with embodiments of the present disclosure. FIG. 1 provides an illustration of only one implementation and does not imply any limitations with regard to the environments in which different embodiments may be implemented. Many modifications to the depicted environment may be made by those skilled in the art without departing from the scope of the invention as recited by the claims.

In embodiments, digitized user symptom system 100 may include data collection devices 102, historical database 108, and patient (e.g., user) data packet 110. In embodiments, data collection devices 102, may include, but are not limited to, wearable devices (e.g., smart watch, smart ring, etc.) and IoT devices (e.g., bio-sensors). In embodiments, data collection devices 102 may collect patient (e.g., user) provided data 104. In embodiments, the user provided data 104 may be stored in historical database 106. In embodiments, Artificial Intelligence Module 108 may analyze both real-time user provided data 104 and historical user provided data, via historical database 106, to digitize user symptoms. In embodiments, digitized user symptom system 100 may be configured to generate a user data packet 110. In embodiments a user data packet may be configured to digitize patient/user symptoms while also aiding authorized users in diagnosing and treating the user symptoms.

Figure 2:
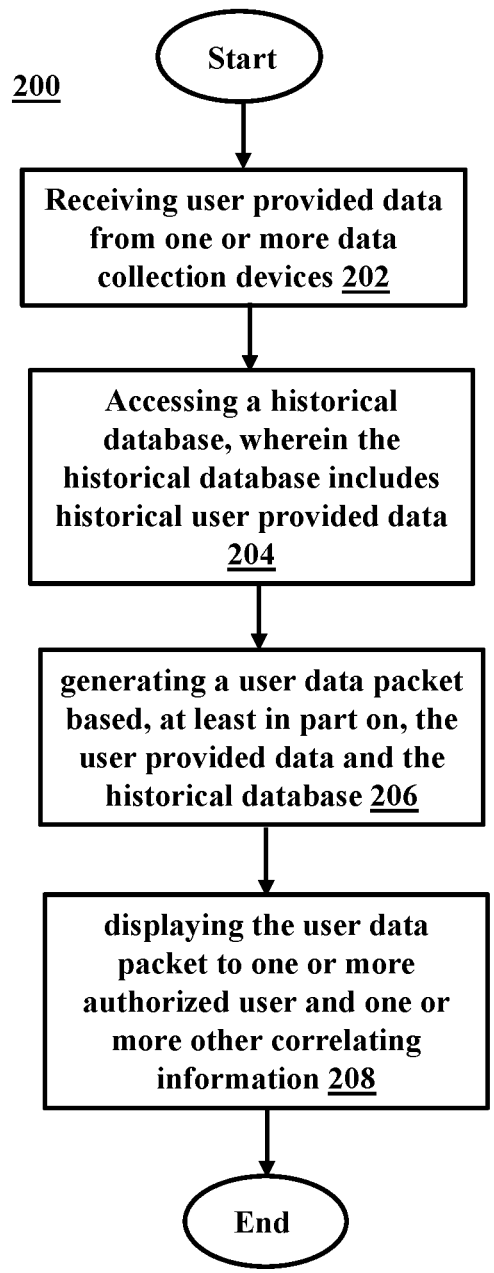
FIG. 2 illustrates a flowchart of a method for digitizing user symptoms, in accordance with embodiments of the present disclosure.

Referring now to FIG. 2, a flowchart illustrating an example method 200 for digitizing user symptoms, in accordance with embodiments of the present disclosure. In some embodiments, the method 200 begins at operation 202 where a processor receives user provided data from one or more data collection devices.

In some embodiments, the method 200 proceeds to operation 204. At operation 204, a processor may access a historical database, wherein the historical database includes historical user provided data.

In some embodiments, the method 200 proceeds to operation 206. At operation 206, the processor may generate a user data packet based, at least in part on, the user provided data and the historical database.

In some embodiments, the method 200 proceeds to operation 208. At operation 208, the processor may display the user data packet to one or more authorized user and one or more other correlating information.

As discussed in more detail herein, it is contemplated that some or all of the operations of the method 200 may be performed in alternative orders or may not be performed at all; furthermore, multiple operations may occur at the same time or as an internal part of a larger process.

It is to be understood that although this disclosure includes a detailed description on cloud computing, implementation of the teachings recited herein are not limited to a cloud computing environment. Rather, embodiments of the present disclosure are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of portion independence in that the consumer generally has no control or knowledge over the exact portion of the provided resources but may be able to specify portion at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 3A:
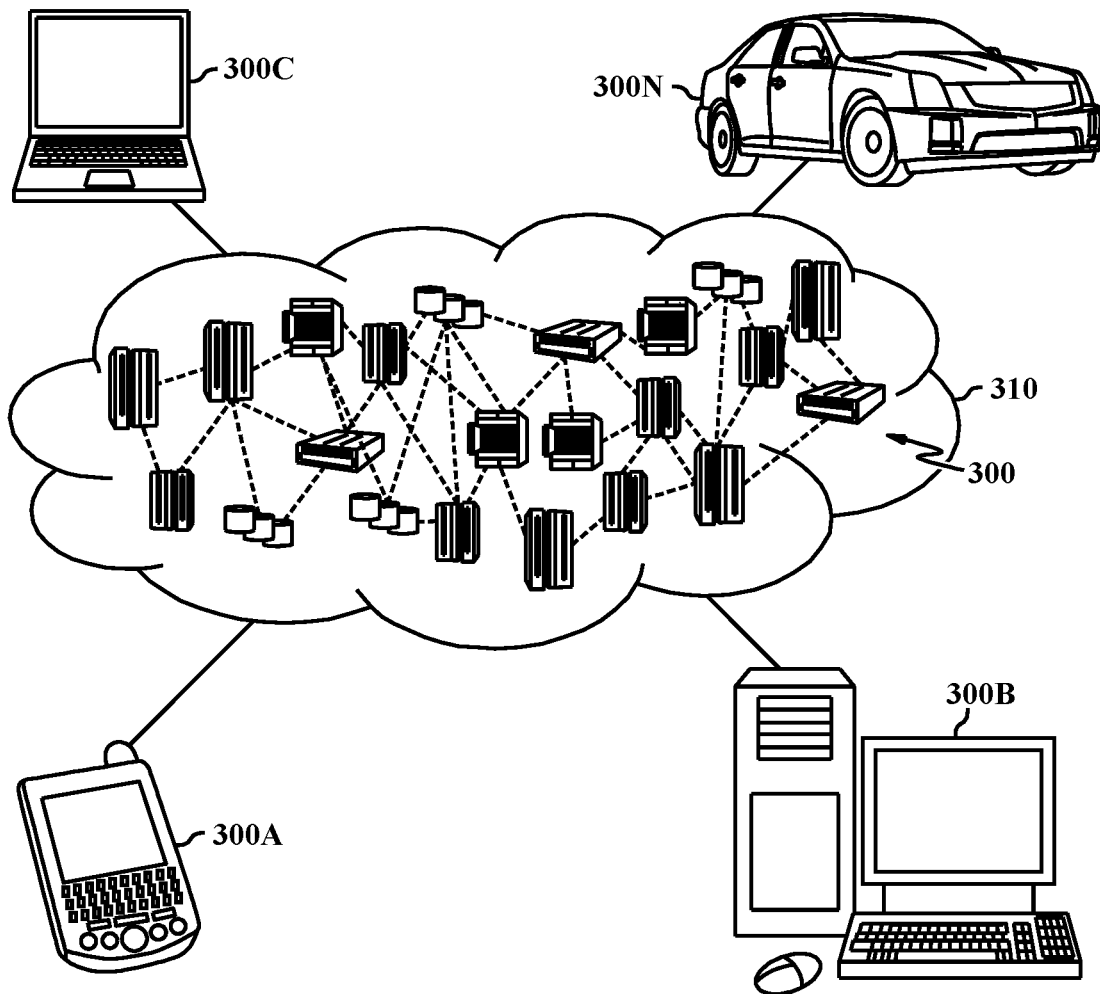
FIG. 3A illustrates a cloud computing environment, in accordance with embodiments of the present disclosure.

Referring now to FIG. 3A, illustrative cloud computing environment 310 is depicted. As shown, cloud computing environment 310 includes one or more cloud computing nodes 300 with which local computing devices used by cloud consumers, such as, for example, personal digital assistant (PDA) or cellular telephone 300A, desktop computer 300B, laptop computer 300C, and/or automobile computer system 300N may communicate. Nodes 300 may communicate with one another. They may be grouped (not shown) physically or virtually, in one or more networks, such as Private, Community, Public, or Hybrid clouds as described hereinabove, or a combination thereof. This allows cloud computing environment 310 to offer infrastructure, platforms and/or software as services for which a cloud consumer does not need to maintain resources on a local computing device. It is understood that the types of computing devices 300A-N shown in FIG. 3A are intended to be illustrative only and that computing nodes 300 and cloud computing 300 and cloud computing environment 310 can communicate with any type of computerized device over any type of network and/or network addressable connection (e.g., using a web browser).

Figure 3B:
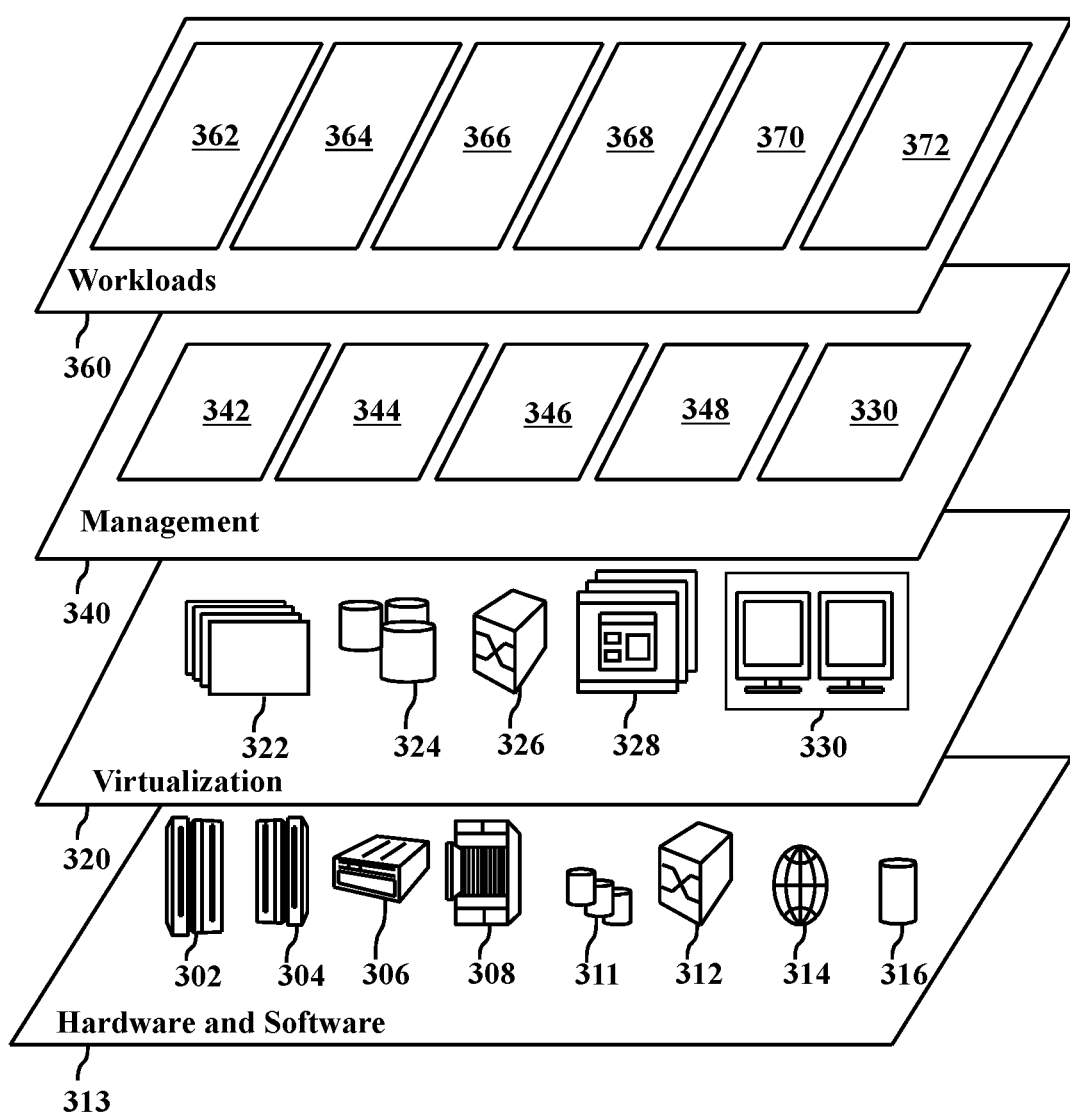
FIG. 3B illustrates abstraction model layers, in accordance with embodiments of the present disclosure.

Referring now to FIG. 3B, a set of functional abstraction layers provided by cloud computing environment 310 (FIG. 3A) is shown. It should be understood in advance that the components, layers, and functions shown in FIG. 3B are intended to be illustrative only and embodiments of the disclosure are not limited thereto. As depicted below, the following layers and corresponding functions are provided.

Hardware and software layer 315 includes hardware and software components. Examples of hardware components include: mainframes 302; RISC (Reduced Instruction Set Computer) architecture based servers 304; servers 306; blade servers 308; storage devices 311; and networks and networking components 312. In some embodiments, software components include network application server software 314 and database software 316.

Virtualization layer 320 provides an abstraction layer from which the following examples of virtual entities may be provided: virtual servers 322; virtual storage 324; virtual networks 326, including virtual private networks; virtual applications and operating systems 328; and virtual clients 330.

In one example, management layer 340 may provide the functions described below. Resource provisioning 342 provides dynamic procurement of computing resources and other resources that are utilized to perform tasks within the cloud computing environment. Metering and Pricing 344 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 346 provides access to the cloud computing environment for consumers and system administrators. Service level management 348 provides cloud computing resource allocation and management such that required service levels are met. Service Level Agreement (SLA) planning and fulfillment 350 provide pre-arrangement for, and procurement of, cloud computing resources for which a future requirement is anticipated in accordance with an SLA.

Workloads layer 360 provides examples of functionality for which the cloud computing environment may be utilized. Examples of workloads and functions which may be provided from this layer include: mapping and navigation 362; software development and lifecycle management 364; virtual classroom education delivery 366; data analytics processing 368; transaction processing 370; and techniques to aid authorized users 372.

Figure 4:
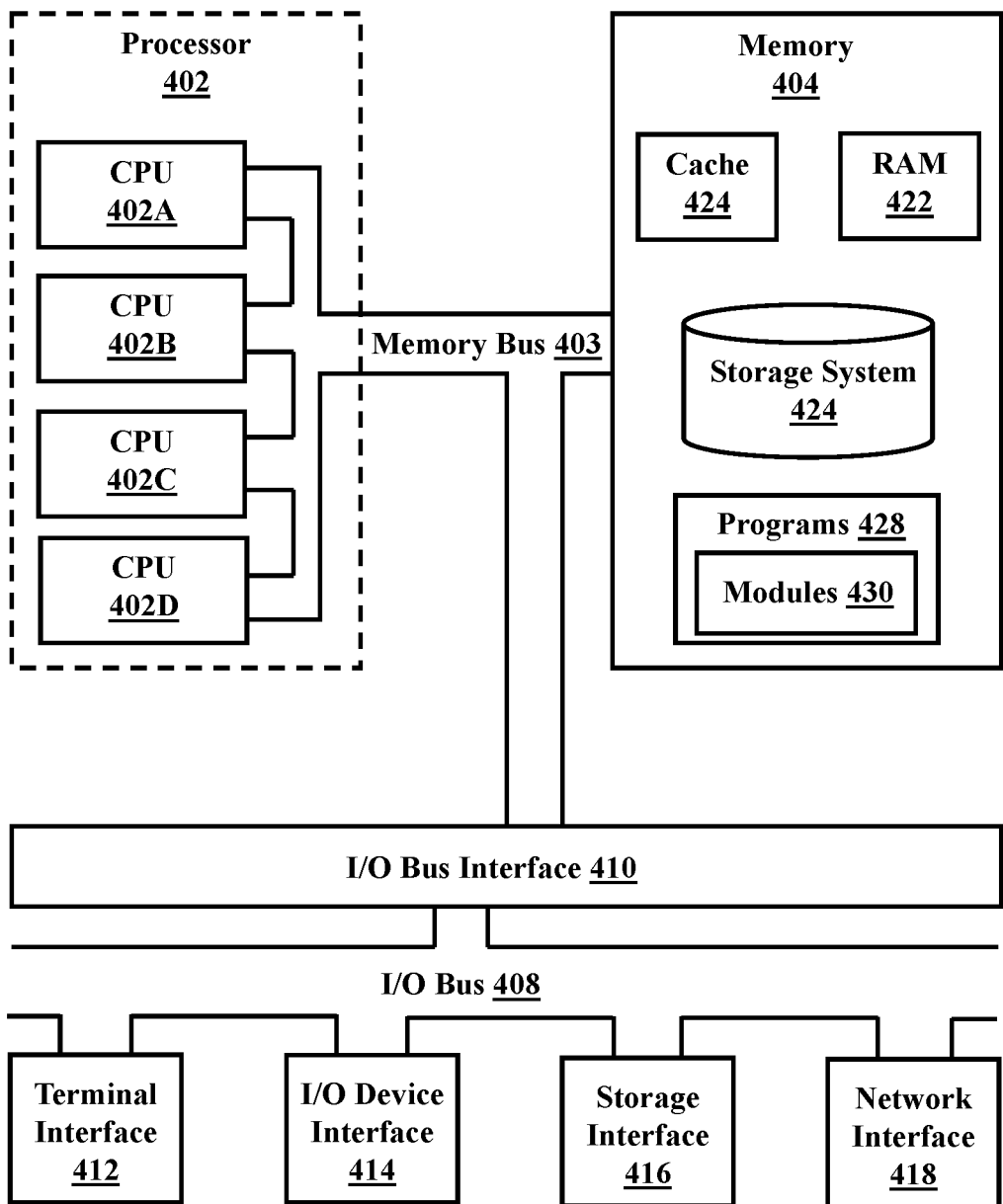
FIG. 4 illustrates a high-level block diagram of an example computer system that may be used in implementing one or more of the methods, tools, and modules, and any related functions, described herein, in accordance with embodiments of the present disclosure.

FIG. 4, illustrated is a high-level block diagram of an example computer system 401 that may be used in implementing one or more of the methods, tools, and modules, and any related functions, described herein (e.g., using one or more processor circuits or computer processors of the computer), in accordance with embodiments of the present invention. In some embodiments, the major components of the computer system 401 may comprise one or more Processor 402, a memory subsystem 404, a terminal interface 412, a storage interface 416, an I/O (Input/Output) device interface 414, and a network interface 418, all of which may be communicatively coupled, directly or indirectly, for inter-component communication via a memory bus 403, an I/O bus 408, and an I/O bus interface unit 410.

The computer system 401 may contain one or more general-purpose programmable central processing units (CPUs) 402A, 402B, 402C, and 402D, herein generically referred to as the CPU 402. In some embodiments, the computer system 401 may contain multiple processors typical of a relatively large system; however, in other embodiments the computer system 401 may alternatively be a single CPU system. Each CPU 402 may execute instructions stored in the memory subsystem 404 and may include one or more levels of on-board cache.

System memory 404 may include computer system readable media in the form of volatile memory, such as random access memory (RAM) 422 or cache memory 424. Computer system 401 may further include other removable/non-removable, volatile/non-volatile computer system storage media. By way of example only, storage system 426 can be provided for reading from and writing to a non-removable, non-volatile magnetic media, such as a "hard drive." Although not shown, a magnetic disk drive for reading from and writing to a removable, non-volatile magnetic disk (e.g., a "floppy disk"), or an optical disk drive for reading from or writing to a removable, non-volatile optical disc such as a CD-ROM, DVD-ROM or other optical media can be provided. In addition, memory 404 can include flash memory, e.g., a flash memory stick drive or a flash drive. Memory devices can be connected to memory bus 403 by one or more data media interfaces. The memory 404 may include at least one program product having a set (e.g., at least one) of program modules that are configured to carry out the functions of various embodiments.

One or more programs/utilities 428, each having at least one set of program modules 430 may be stored in memory 404. The programs/utilities 428 may include a hypervisor (also referred to as a virtual machine monitor), one or more operating systems, one or more application programs, other program modules, and program data. Each of the operating systems, one or more application programs, other program modules, and program data or some combination thereof, may include an implementation of a networking environment. Programs 428 and/or program modules 430 generally perform the functions or methodologies of various embodiments.

Although the memory bus 403 is shown in FIG. 4 as a single bus structure providing a direct communication path among the CPUs 402, the memory subsystem 404, and the I/O bus interface 410, the memory bus 403 may, in some embodiments, include multiple different buses or communication paths, which may be arranged in any of various forms, such as point-to-point links in hierarchical, star or web configurations, multiple hierarchical buses, parallel and redundant paths, or any other appropriate type of configuration. Furthermore, while the I/O bus interface 410 and the I/O bus 408 are shown as single respective units, the computer system 401 may, in some embodiments, contain multiple I/O bus interface units 410, multiple I/O buses 408, or both. Further, while multiple I/O interface units are shown, which separate the I/O bus 408 from various communications paths running to the various I/O devices, in other embodiments some or all of the I/O devices may be connected directly to one or more system I/O buses.

In some embodiments, the computer system 401 may be a multi-user mainframe computer system, a single-user system, or a server computer or similar device that has little or no direct user interface, but receives requests from other computer systems (clients). Further, in some embodiments, the computer system 401 may be implemented as a desktop computer, portable computer, laptop or notebook computer, tablet computer, pocket computer, telephone, smartphone, network switches or routers, or any other appropriate type of electronic device.

It is noted that FIG. 4 is intended to depict the representative major components of an exemplary computer system 401. In some embodiments, however, individual components may have greater or lesser complexity than as represented in FIG. 4, components other than or in addition to those shown in FIG. 4 may be present, and the number, type, and configuration of such components may vary.

As discussed in more detail herein, it is contemplated that some or all of the operations of some of the embodiments of methods described herein may be performed in alternative orders or may not be performed at all; furthermore, multiple operations may occur at the same time or as an internal part of a larger process.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

Although the present invention has been described in terms of specific embodiments, it is anticipated that alterations and modification thereof will become apparent to the skilled in the art. Therefore, it is intended that the following claims be interpreted as covering all such alterations and modifications as fall within the true spirit and scope of the disclosure.

What is claimed is:

1. A computer-implemented method, the method comprising:
   receiving, by a processor, user provided data from one or more data collection devices;
   accessing a historical database, wherein the historical database includes historical user provided data;
   generating a user data packet based, at least in part on, the user provided data and the historical database by:
      selecting portions of the user provided data and/or the historical user provided data that correspond to a medical discipline associated with one or more authorized users, and
      using the selected portions of the user provided data and/or the historical database to generate a user data packet for the one or more authorized users;
   generating one or more simulations using the user data packet;
   generating a video snippet associated with the user from the one or more simulations; and
   displaying to the one or more authorized users: the video snippet, and one or more reports summarizing medical information corresponding to one or more other users having symptoms that overlap the user provided data.

2. The computer-implemented method of claim 1, wherein the displaying to one or more authorized users: the video snippet, and one or more reports, includes:
   recommending one or more diagnoses associated with the user's symptoms.

3. The computer-implemented method of claim 2, wherein displaying the user data packet to one or more authorized user includes:
   generating one or more treatment plans associated with the one or more diagnoses.

4. The computer-implemented method of claim 1, further comprising:
   receiving user provided data.

5. The computer-implemented method of claim 1, wherein displaying the user data packet to one or more authorized user includes:
   displaying a cross-sectional study, wherein the cross-sectional study includes comparing the user symptoms to another user symptoms.

6. The computer-implemented method of claim 1, wherein user provided data from one or more data collection devices is collected from wearable devices.

7. A system, the system comprising:
a memory; and
a processor in communication with the memory, the processor being configured to perform operations comprising:
receiving user provided data from one or more data collection devices;
accessing a historical database, wherein the historical database includes historical user provided data;
generating a user data packet based, at least in part on, the user provided data and the historical database;
generating one or more simulations using the user data packet;
generating a video snippet associated with the user from the one or more simulations and/or the user data packet; and
simultaneously displaying to one or more authorized users: the video snippet, and one or more reports summarizing medical information corresponding to one or more other users having symptoms that overlap the user provided data,
wherein the generating of the user data packet includes, for each of the one or more authorized users:
selecting portions of the user provided data and/or the historical user provided data that correspond to a medical discipline associated with a given one of the authorized users; and
using the selected portions of the user provided data and/or the historical database to generate a user data packet for the given one of the authorized users,
wherein the simultaneously displaying to one or more authorized users: the video snippet, and one or more reports, includes:
generating one or more treatment plans associated with the one or more diagnoses.

8. The system of claim 7, wherein displaying the user data packet to one or more authorized user includes:
recommending one or more diagnoses associated with the user's symptoms.

9. The system of claim 7, further comprising:
receiving user provided data.

10. The system of claim 7, wherein displaying the user data packet to one or more authorized user includes:
displaying a cross-sectional study, wherein the cross-sectional study includes comparing the user symptoms to another user symptoms.

11. The system of claim 7, wherein user provided data from one or more data collection devices is collected from wearable devices.

12. A computer program product, the computer program product comprising a computer readable storage medium having program instructions embodied therewith, the program instructions executable by a processor to cause the processors to perform a function, the function comprising:
receiving user provided data from one or more data collection devices;
accessing a historical database, wherein the historical database includes historical user provided data;
generating user data packets for authorized users by:
selecting portions of the user provided data and/or the historical user provided data that correspond to a medical discipline associated with a given one of the authorized users, and
using the selected portions of the user provided data and/or the historical database to generate a user data packet for the given one of the authorized users;
generating one or more simulations using the user data packet;
generating a video snippet associated with the user from the one or more simulations and/or the user data packet; and
displaying to the authorized users: the video snippet, and one or more reports summarizing medical information corresponding to one or more other users having symptoms that overlap the user provided data.

13. The computer program product of claim 12, wherein displaying the user data packet to one or more authorized user includes:
recommending one or more diagnoses associated with the user's symptoms.

14. The computer program product of claim 13, wherein displaying the user data packet to one or more authorized user includes:
generating one or more treatment plans associated with the one or more diagnoses.

15. The computer program product of claim 12, further comprising:
receiving user provided data.

16. The computer program product of claim 12, wherein displaying the user data packet to one or more authorized user includes:
displaying a cross-sectional study, wherein the cross-sectional study includes comparing the user symptoms to another user symptoms.

* * * * *